（12） United States Patent
Tashev et al.

(10) Patent No.: US 10,528,147 B2
(45) Date of Patent: Jan. 7, 2020

(54) ULTRASONIC BASED GESTURE RECOGNITION

(71) Applicant: Microsoft Technology Licensing, LLC, Redmond, WA (US)

(72) Inventors: Ivan Jelev Tashev, Kirkland, WA (US); Shuayb Zarar, Redmond, WA (US); Amit Das, Champaign, IL (US)

(73) Assignee: Microsoft Technology Licensing, LLC, Redmond, WA (US)

(*) Notice: Subject to any disclaimer, the term of this patent is extended or adjusted under 35 U.S.C. 154(b) by 196 days.

(21) Appl. No.: 15/640,327

(22) Filed: Jun. 30, 2017

(65) Prior Publication Data

US 2017/0300124 A1    Oct. 19, 2017

Related U.S. Application Data

(60) Provisional application No. 62/467,741, filed on Mar. 6, 2017.

(51) Int. Cl.
*G06F 3/01* (2006.01)
*A61K 8/97* (2017.01)
(Continued)

(52) U.S. Cl.
CPC ............... *G06F 3/017* (2013.01); *A61K 8/97* (2013.01); *A61K 36/15* (2013.01); *A61Q 19/00* (2013.01);
(Continued)

(58) Field of Classification Search
CPC combination set(s) only.
See application file for complete search history.

(56) References Cited

U.S. PATENT DOCUMENTS 4,752,896 A    6/1988  Matsumoto
8,323,106 B2  12/2012  Zalewski
(Continued)

FOREIGN PATENT DOCUMENTS

CN    103559888 A    2/2014
CN    104751855 A    7/2015
WO    2008145952 A1  12/2008

OTHER PUBLICATIONS

Lee, D D., et al., "Algorithms for nonnegative matrix factorization", In Proceedings of the 13th International Conference on Neural Information Processing Systems, Dec. 2001, pp. 535-541.
(Continued)

*Primary Examiner* — Tsung Yin Tsai
(74) *Attorney, Agent, or Firm* — Drinker Biddle & Reath LLP

(57) ABSTRACT

An ultrasonic gesture recognition system is provided that recognizes gestures based on analysis of return signals of an ultrasonic pulse that is reflected from a gesture. The system transmits an ultrasonic chirp and samples a microphone array at sample intervals to collect a return signal for each microphone. The system then applies a beamforming technique to frequency domain representations of the return signals to generate an acoustic image with a beamformed return signal for multiple directions. The system then generates a feature image from the acoustic images to identify, for example, distance or depth from the microphone array to the gesture for each direction. The system then submits the feature image to a deep learning system to classify the gesture.

12 Claims, 9 Drawing Sheets

US 10,528,147 B2
Page 2

(51) Int. Cl.
 *A61Q 19/00*  (2006.01)
 *A61K 36/15*  (2006.01)
 *G06K 9/62*  (2006.01)
 *G06N 3/04*  (2006.01)

(52) U.S. Cl.
 CPC ......... *G06K 9/6267* (2013.01); *G06N 3/0445* (2013.01)

(56) References Cited

U.S. PATENT DOCUMENTS

| | | | |
|---|---|---|---|
| 8,907,929 | B2 | 12/2014 | Li et al. |
| 9,019,201 | B2* | 4/2015 | Holmdahl .......... G06K 9/00342 345/156 |
| 9,668,066 | B1 | 5/2017 | Betts et al. |
| 9,911,290 | B1* | 3/2018 | Zalewski ............. G07G 1/0072 |
| 10,042,038 | B1* | 8/2018 | Lord ........................ G01S 5/26 |
| 2011/0096954 | A1* | 4/2011 | Dahl ....................... G06F 3/017 382/103 |
| 2012/0001875 | A1* | 1/2012 | Li .......................... G01S 7/5273 345/177 |
| 2012/0206339 | A1* | 8/2012 | Dahl ....................... G06F 3/043 345/156 |
| 2014/0229168 | A1 | 8/2014 | Pandya |
| 2015/0025880 | A1 | 1/2015 | Le roux et al. |
| 2015/0112670 | A1 | 4/2015 | Le roux et al. |
| 2015/0154035 | A1 | 6/2015 | Lepeniuk et al. |
| 2015/0243284 | A1 | 8/2015 | Guo et al. |
| 2016/0071526 | A1* | 3/2016 | Wingate ................ G10L 21/028 704/233 |
| 2016/0099008 | A1 | 4/2016 | Barker et al. |
| 2016/0111107 | A1 | 4/2016 | Erdogan et al. |
| 2016/0241346 | A1 | 8/2016 | Hoffman |
| 2016/0284346 | A1 | 9/2016 | Visser et al. |
| 2016/0300361 | A1 | 10/2016 | Xie et al. |
| 2016/0313801 | A1* | 10/2016 | Wagner .................... G06F 3/017 |
| 2017/0060254 | A1* | 3/2017 | Molchanov ............. G06F 3/011 |
| 2017/0150235 | A1* | 5/2017 | Mei .................... H04N 21/8405 |
| 2017/0162194 | A1 | 6/2017 | Nesta et al. |
| 2017/0168158 | A1* | 6/2017 | Reining .............. G01S 7/52004 |
| 2018/0254050 | A1 | 9/2018 | Tashev et al. |

OTHER PUBLICATIONS

Lee, Y D., et al., "Wireless sensor network based wearable smart shirt for ubiquitous health and activity monitoring", In Journal of Sensors and Actuators B: Chemical, vol. 140, Issue 2, Jul. 2009, pp. 390-395.

Li, D, et al., "Boosting accuracy of attribute prediction via SVD and NMF of instance-attribute matrix", In Proceedings of Pacific Rim Conference on Multimedia, Dec. 15, 2015, pp. 466-476.

Liolios, C, et al., "An overview of body sensor networks in enabling pervasive healthcare and assistive environments", In Proceedings of the 3rd International Conference on PErvasive Technologies Related to Assistive Environments, Jun. 23, 2010, 10 Pages.

Manninia, A, et al., "Accelerometer based recognition of the placement sites of a wearable sensor", In Journal of Pervasive and Mobile Computing, vol. 21, Aug. 1, 2015, pp. 62-74.

Mathie, M J., et al., "Accelerometry: Providing an integrated, practical method for long-term, ambulatory monitoring of human movement", In Proceedings of Physiological Measurement, vol. 25, Issue: 2, May 2004, 21 Pages.

Mejia-Roa, et al., "NMF-mGPU: non-negative matrix factorization on multi-GPU systems", In Journal of BMC Bioinformatics, Feb. 13, 2015, pp. 1-12.

Mohammadiha, et al., "Supervised and unsupervised speech enhancement using nonnegative matrix factorization", In Journal of IEEE Transactions on Audio, Speech, and Language Processing, vol. 21, No. 10, Oct. 21, 2013, pp. 1-12.

Mohammed, Shoaib, et al., "A Statistical Approach to Semi-Supervised Speech Enhancement With Low-Order Non-Negative Matrix Factorization", In Proceedings of IEEE International Conference on Acoustics, Speech and Signal Processing (ICASSP), Mar. 5, 2017, 5 Pages.

Mohammed, Shoaib, et al., "Unsupervised Deep Representation Learning to Remove Motion Artifacts in Free-mode Body Sensor Networks", In Proceedings of 2017 IEEE 14th International Conference on Wearable and Implantable Body Sensor Networks (BSN), May 9, 2017, 6 pages.

Moore, S T., et al., "Long-term monitoring of gait in parkinson's disease", In Journal of Gait Posture, vol. 26, Issue 2, Jul. 2007, 8 Pages.

Mysore, G J., "A block sparsity approach to multiple dictionary learning for audio modeling", In Proceedings of International Workshop on Sparsity, Dictionaries, Projections, Machine Learning, and Signal Processing, Jun. 2012, 4 Pages.

Mysore, G J., et al., "A non-negative approach to semi-supervised separation of speech from noise with the use of temporal dynamics", In Proceedings of IEEE International Conference on Acoustics, Speech and Signal Processing (ICASSP), May 2011, pp. 17-20.

Nordic Semiconductors, "nRF8001 bluetooth low energy connectivity IC", Retrieved From: https://www.nordicsemi.com/Products/, Retrieved Date: Jan. 1, 2017, 7 Pages.

Ordonez, F J., et al., "Deep convolutional and LSTM recurrent neural networks for multimodal wearable activity recognition", In Journal of Sensors, vol. 16, Issue 1, Jan. 18, 2016, pp. 115-130.

"International Search Report and Written Opinion Issued in PCT Application No. PCT/US2018/019796", dated Aug. 30, 2018, 18 Pages.

"International Search Report and Written Opinion Issued in PCT Application No. PCT/US2018/019796", dated Aug. 7, 2018, 17 Pages.

Roux, J L., et al., "Ensemble learning for speech enhancement", In proceedings of IEEE Workshop on Applications of Signal Processing to Audio and Acoustics, Oct. 20, 2013, pp. 1-4.

Roux, J L., et al., "Sparse NMF—half-baked or well done?", In Proceedings of Mitsubishi Electric Research Laboratories (MERL), Rep. No. TR2015-023, Mar. 2015, 23 Pages.

Rusu, C, et al., "Perceptual evaluation of speech quality (PESQ): A new method for speech quality assessment of telephone networks and codecs", In Proceedings of 2001 IEEE International Conference on Acoustics, Speech, and Signal Processing, May 7, 2001, 4 Pages.

Sigg, et al., "Speech Enhancement Using Generative Dictionary Learning", In Proceedings of IEEE Transactions on Audio, Speech, and Language Processing, vol. 20, Issue 6, Aug. 2012, pp. 1698-1712.

Sprechmann, et al., "Supervised Non-Euclidean Sparse Nmf Via Bilevel Optimization With Applications To Speech Enhancement", In Proceedings of 4th Joint Workshop on Hands-free Speech Communication and Microphone Arrays, May 12, 2014, pp. 11-15.

St Microelectronics, "LSM9DSO iNEMO inertial module:3D accelerometer, 3D gyroscope, 3D magnetometer", Retrieved From: https://www.st.com/resource/en/datasheet/lsm9ds1.pdf, Retrieved On: Jan. 1, 2017, 72 Pages.

Sun, D L., et al., "Universal speech models for speaker independent single channel source separation", In Proceedings of IEEE International Conference on Acoustics, Speech and Signal Processing, May 2013, pp. 141-145.

Texas Instruments, "TCA9548A: Low-voltage 8-channel I2C switch", Retrieved From: http://www.ti.com/product/TCA9548A, Retrieved Date: Jan. 1, 2017, 3 Pages.

Varga, A, et al., "Assessment for automatic speech recognition: II. NOISEX-92: A database and an experiment to study the effect of additive noise on speech recognition systems", In Proceedings of Speech Communication, vol. 12, Issue 3, Jul. 1993, pp. 247-251.

Vincent, et al., "Performance measurement in blind audio source separation", In Journal of IEEE Transactions on Audio, Speech, and Language Processing, vol. 14, Issue 4, Jul. 2006, pp. 1462-1469.

Virtanen, T, "Monaural sound source separation by nonnegative matrix factorization with temporal continuity and sparseness criteria", In proceedings of IEEE Transactions on Audio, Speech, and Language Processing, vol. 15, Issue: 3, Mar. 2007, pp. 1066-1074.

(56) References Cited

OTHER PUBLICATIONS

Wainwright, M J., et al., "Graphical models, exponential families, and variational inference", In Journal of Foundations and Trends in Machine Learning, vol. 1, Issue 1-2, Jan. 2008, pp. 1-305.

Weninger, et al., "Non-negative matrix factorization for highly noise-robust asr:To enhance or to recognize?", In Proceedings of IEEE International Conference on Acoustics, Speech and Signal Processing, Mar. 25, 2012, pp. 4681-4684.

Wild, S, et al., "Improving nonnegative matrix factorizations through structured initialization", In Proceedings of Pattern Recognition, vol. 37, Issue 11, Nov. 2004, pp. 2217-2232.

Xue, Y, et al., "Clustering-based initialization for non-negative matrix factorization", In Proceedings of Applied Mathematics and Computation, vol. 205, Issue 2, Nov. 15, 2008, pp. 525-536.

Zhang, Z, et al., "A survey of sparse representation: Algorithms and applications", In Proceedings of IEEE Access, vol. 3, May 2015, pp. 490-530.

Zheng, Z, et al., "Initialization enhancer for non-negative matrix factorization", In Proceedings of Engineering Applications of Artificial Intelligence, vol. 20, Issue 1, Feb. 2007, pp. 101-110.

"Opportunity human activity recognition challenge dataset 2012", Retrieved From: https://web.archive.org/web/20170404100301/http://www.opportunity-project.eu/challengeDataset, Retrieved On: Jan. 1, 2017, 3 Pages.

"Final Office Action Issued in U.S. Appl. No. 15/626,016", dated Jun. 12, 2018, 31 Pages.

"Non Final Office Action Issued in U.S. Appl. No. 15/626,016", dated Mar. 30, 2018, 26 Pages.

"Notice of Allowance Issued in U.S. Appl. No. 15/626,016", dated Oct. 2, 2018, 16 Pages.

Alinia, P, et al., "Impact of sensor misplacement on estimating metabolic equivalent of task with wearables", In Proceedings of 2015 IEEE 12th International Conference on Wearable and Implantable Body Sensor Networks (BSN), Jun. 9, 2015, 6 Pages.

Atmel, "ATmega32U4 low power 8-bit AVR RISC microcontroller", Retrieved From: http://www.atmel.com/devices/atmega32u4.aspx, Retrieved Date: Jan. 1, 2017, 3 Pages.

Baby, et al., "Coupled Dictionary Training for Exemplar-Based Speech Enhancement", In Proceedings of IEEE International Conference on Acoustics, Speech and Signal Processing, May 4, 2004, pp. 2883-2887.

Baraniuk, R G., et al., "Applications of sparse representation and compressive sensing", In Proceedings of the IEEE, vol. 98 , Issue: 6, Jun. 2010, pp. 906-909.

Bergmann, J H. M.., et al., "An attachable clothing sensor system for measuring knee joint angles", In Proceedings of IEEE Sensors Journal, vol. 13 , Issue: 10, Oct. 2013, pp. 4090-4097.

Bhiksha, Raj, et al., "Ultrasonic Doppler Sensing in HCI", In Proceedings of IEEE Pervasive Computing, vol. 11 , Issue: 2, Feb. 1, 2012, pp. 24-29.

Cao, H, et al., "Enabling technologies for wireless body area networks: A survey and outlook", In Proceedings of IEEE Communications Magazine, vol. 47, Issue: 12, Dec. 2009, pp. 84-93.

Catrysse, M, et al., "Towards the integration of textile sensors in a wireless monitoring suit", In Journal of Sensors and Actuators A: Physical, vol. 114, Issue 2, Sep. 2004, pp. 302-311.

Chavarriaga, R, et al., "The opportunity challenge: A benchmark database for on-body sensor-based activity recognition", In Journal of Pattern Recognition Letters, vol. 34, Issue 15, Nov. 2013, pp. 2033-2042.

Chen, M, et al., "Body area networks: A survey", In Journal of Mobile Networks and Applications, vol. 16, Issue 2, Apr. 2011, pp. 171-193.

Chen, et al., "Speaker Recognition of Noisy Short Utterance Based on Speech Frame Quality Discrimination and Three-stage Classification Model", In International Journal of Control and Automation, vol. 8, Issue 3, Mar. 2015, pp. 135-146.

Das, Amit, et al., "Ultrasound based gesture recognition", In Proceedings of 2017 IEEE International Conference on Acoustics, Speech and Signal Processing (ICASSP), Mar. 5, 2017, pp. 406-410.

Dokmanic, Ivan, et al., "Hardware and algorithms for ultrasonic depth imaging", In Proceedings of 2014 IEEE International Conference on Acoustics, Speech and Signal Processing (ICASSP), May 4, 2014, pp. 6702-6706.

Eleni, Tsironi, et al., "Gesture Recognition with a Convolutional Long Short-Term Memory Recurrent Neural Network", In Proceedings of the European Symposium on Artificial Neural Networks, Computational Intelligence and Machine Learning (ESANN), Apr. 27, 2016, 6 Pages.

Enokibori, Y, et al., "A study of intermittent adjustment to resist displacement of smart garment using posture-stable daily actions", In Proceedings of UbiComp/ISWC Adjunct, Sep. 7, 2015, 4 Pages.

Ephraim, et al., "Speech enhancement using a minimum-mean square error short-time spectral amplitude estimator", In Journal of IEEE Transactions on Acoustics, Speech, and Signal Processing, vol. 32, Issue 6, Dec. 1984, pp. 1109-1121.

Fan, et al., "Speech enhancement using segmental nonnegative matrix Factorization", In Proceedings of IEEE International Conference on Acoustics, Speech and Signal Processing, May 9, 2014, pp. 4483-4487.

Freund, Yoav, "A Decision-Theoretic Generalization of On-Line Learning and an Application to Boosting", In Journal of Computer and System Sciences, vol. 55, Issue 1, Aug. 1997, pp. 119-139.

Garofolo, J S., et al., "TIMIT acoustic-phonetic continuous speech corpus", In Proceedings of Linguistic Data Consortium, Jan. 1993, 95 Pages.

Gioberto, G, et al., "Garment positioning and drift in garment-integrated wearable sensing", In Proceedings of 2012 16th International Symposium on Wearable Computers, Jun. 18, 2012, pp. 64-71.

Grais, E M., et al., "Initialization of nonnegative matrix factorization dictionaries for single channel source separation", In Proceedings of 21st Signal Processing and Communications Applications Conference (SIU), Apr. 24, 2013, pp. 1-4.

Grais, E M., et al., "Spectro-temporal post-smoothing in NMF based single-channel source separation", In Proceedings of Proceedings of the 20th European Signal Processing Conference (EUSIPCO), Aug. 27, 2012, pp. 584-588.

Greene, D, et al., "Ensemble non-negative matrix factorization methods for clustering protein-protein interactions", In Journal of Bioinformatics, vol. 24, Issue 15, Aug. 1, 2008, pp. 1722-1728.

Hirsch, et al., "The Aurora experimental framework for the performance evaluation of speech recognition systems under noisy conditions", In Proceedings of Automatic Speech Recognition: Challenges for the new Millenium ISCA Tutorial and Research Workshop, Sep. 18, 2000, 8 Pages.

Hoyer, P.O., "Non-negative matrix factorization with sparseness constraints", In the Journal of Machine Learning Research, vol. 5, Nov. 2004, pp. 1457-1469.

Incel, O.D., "Analysis of movement, orientation and rotation-based sensing for phone placement recognition", In Journal of Sensors (Basel), vol. 15, Issue 10, Oct. 5, 2015, pp. 25474-25506.

Invensense, "MPU-9150: Nine-axis MEMS motion tracking device", Retrieved From: https://www.invensense.com/products/motion-tracking/9-axis/mpu-9150/, Retrieved on: Jan. 1, 2017, 5 Pages.

Jaureguiberry, X, et al., "Adaptation of source-specific dictionaries in non-negative matrix factorization for source separation", In Proceedings of IEEE International Conference on Acoustics, Speech and Signal Processing (ICASSP), May 22, 2011, pp. 5-8.

Kannan, et al., "A High-Performance Parallel Algorithm for Non-negative Matrix", In Proceedings of the 21st ACM SIGPLAN Symposium on Principles and Practice of Parallel Programming, Mar. 12, 2016, 11 Pages.

Kim, Y D., et al., "A method of initialization for non-negative matrix factorization", In Proceedings of IEEE International Conference on Acoustics, Speech and Signal Processing—ICASSP '07, Apr. 15, 2007, pp. 533-537.

(56) References Cited

OTHER PUBLICATIONS

Kim, M, et al., "Mixtures of local dictionaries for unsupervised speech enhancement", In Proceedings of IEEE Signal Processing Letters, vol. 22, Issue: 3, Mar. 2015, pp. 293-297.

King, B, et al., "Single-channel source separation using simplified-training complex matrix factorization", In Proceedings of IEEE International Conference on Acoustics, Speech and Signal Processing, Mar. 14, 2010, pp. 1206-4209.

Kingma, D P., et al., "Auto-encoding variational bayes", In Proceedings of International Conference Learning and Representation, Dec. 2013, pp. 13-21.

Koitka, et al., "nmfgpu4R: GPU-Accelerated Computation of the Non-Negative Matrix Factorization (NMF) Using CUDA Capable Hardware", In the R Journal, vol. 8, Issue 2, Dec. 2016, pp. 1-11.

Kunze, K, et al., "Sensor placement variations in wearable activity recognition", In Proceedings of IEEE Pervasive Computing, vol. 13, Issue: 4, Oct. 2014, pp. 32-41.

Lapinski, M, et al., "A distributed wearable, wireless sensor system for evaluating professional baseball pitchers and batters", In Proceedings of 2009 International Symposium on Wearable Computers, Sep. 4, 2009, 9 Pages.

Molchanov, et al., "Multi-sensor System for Driver's Hand-Gesture Recognition", In Proceedings of the 11th IEEE International Conference and Workshops on Automatic Face and Gesture Recognition, May 4, 2015, 8 pages.

Periverzov, et al., "3D Imaging for Hand Gesture Recognition: Exploring the Software-Hardware Interaction of Current Technologies", In Journal of 3D Research, vol. 3 Issue 3, Sep. 2012, pp. 1-30.

Mujibiya, et al., "The Sound of Touch: On-body Touch and Gesture Sensing Based on Transdermal Ultrasound Propagation", In Proceedings of the ACM international conference on Interactive tabletops and surfaces, Oct. 6, 2013, pp. 189-198.

Chochai, et al., "Real-time gesture recognition with finger naming by RGB camera and IR depth sensor", In Proceedings of IEEE International Conference on Robotics and Biomimetics (ROBIO), Dec. 5, 2014, pp. 931-936.

Kapuscinski, et al., "Recognition of Hand Gestures Observed by Depth Cameras", In International Journal of Advanced Robotic Systems, Apr. 14, 2015, pp. 1-15.

Palacios, et al., "Human-Computer Interaction Based on Hand Gestures Using RGB-D Sensors", In Journal of Sensors, vol. 13, Issue 9, Sep. 6, 2013, 27 pages.

Bergh, et al., "Combining RGB and ToF Cameras for Real-time 3D Hand Gesture Interaction", In Proceedings of IEEE Workshop on Applications of Computer Vision, Jan. 5, 2011, 7 pages.

Liu, et al., "SoundSense: 3D Gesture Sensing using Ultrasound on Mobile Devices", https://www.google.co.in/url?sa=t&rct=j&q=&esrc=s&source=web&cd=1&cad=rja&uact=8&ved=0ahUKEwiY98q_sezSAhVBMY8KHZcODAsQFggbMAA&url=http%3A%2F%2Fmrorz.github.io%2Ffiles%2Fsoundsense.pdf&usg=AFQjCNHsOH27SIK2Np9X4O1q87YzSOykdQ, Retrieved on: Mar. 23, 2017, 7 pages.

"Elliptic Labs", http://www.ellipticlabs.com/home/, Retrieved on: Mar. 23, 2017, 6 pages.

"Ultrasonic Gesture Recognition", https://swarmlab.eecs.berkeley.edu/projects/4684/ultrasonic-gesture-recognition, Retrieved on: Mar. 23, 2017, 2 pages.

\* cited by examiner

ULTRASONIC BASED GESTURE RECOGNITION

CROSS-REFERENCE TO RELATED APPLICATION

This application claims the benefit of U.S. Provisional Application No. 62/467,741, filed on Mar. 6, 2017, which is hereby incorporated by reference in its entirety.

BACKGROUND

Mobile interactive devices are emerging as the next frontier of personalized computing. Such mobile interactive devices include head-mounted displays ("HMDs") (e.g., supporting augmented reality) and wearable devices. The widespread adoption of such devices will depend on providing effective input-output ("IO") modalities such as gestures, touch, and voice. A challenge is providing gesture recognition for mobile, interactive devices. Current technologies employ optical sensing for gesture recognition. Such technologies rely on estimating distances to target objects by measuring the time of flight ("ToF") in air. ToF is the duration between the time a probe signal is transmitted to the target object and the time the reflected version of the probe signal is received. It is measured as $$\frac{2d}{c},$$

where d is the distance of the target object and $c=2.998 \times 10^8$ m/s is the speed of light in air.

Although optical sensors are effective at gesture recognition, they face high-energy costs because of illumination overhead and processing complexities (e.g., capture, synchronization, and analysis). The high energy costs limit their use in mobile interactive devices where energy costs carry a big premium in large part because of the weight and size of the battery. For example, an HMD running on a 1500 mAH (3.8 V) battery may have an IO energy budget of 20% (i.e., 4104 J). If an optical sensor consumes 2.5 W of power, the HMD can support about 500 gestures with each gesture lasting 3 seconds (e.g., IO budget/energy-per-gesture=4104 J/7.5 J).

SUMMARY

An ultrasonic gesture recognition ("UGR") system is provided that recognizes gestures based on analysis of return signals from an ultrasonic pulse that are reflected from a gesture. The UGR system may transmit an ultrasonic chirp and collect samples at sample intervals via a microphone array. The samples for a microphone form a return signal for the microphone. The UGR system then uses a beamforming technique to generate an acoustic image for the chirp from the return signals. The acoustic image contains, for multiple directions, an estimated frequency domain return signal that is estimated to have been reflected from the gesture in that direction. The UGR system then generates a feature image from the acoustic images to identify, for example, distance or depth from the microphone to the gesture for each direction. The UGR system then submits the feature image to a deep learning system to classify the gesture.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Figure 1:
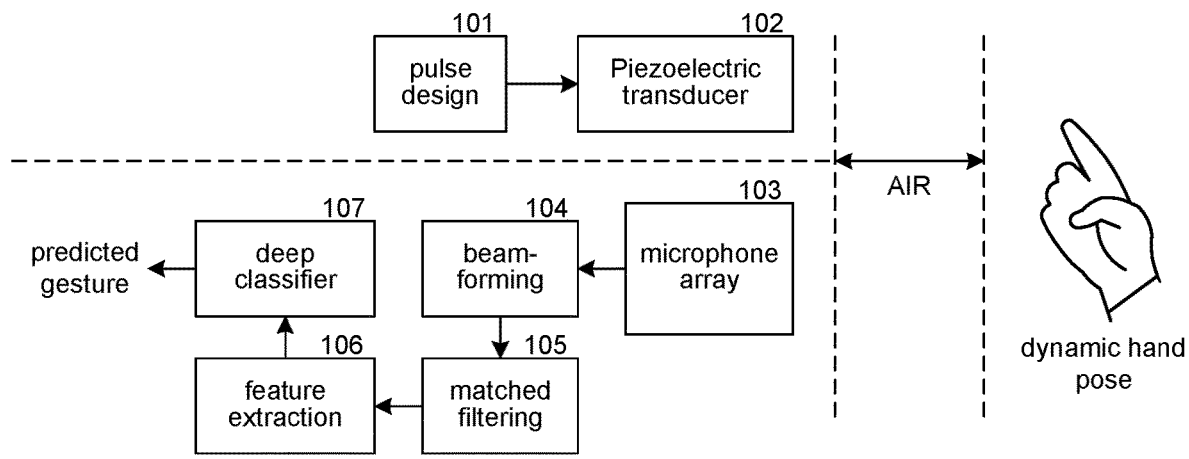
FIG. 1 is a block diagram illustrating an architecture of the UGR system in some embodiments.

A method and system for recognizing gestures based on ultrasonic signals and a deep learning network is provided. In some embodiments, an ultrasonic-based gesture recognition ("UGR") system transmits via a transmitter an ultrasonic signal of varying frequencies (e.g., a chirp) to receive return signals from the gesture. For example, the gesture may be a static gesture (e.g., an OK gesture) or a dynamic gesture (e.g., a tap, a bloom, or a sign language gesture). The UGR system then receives the return signals of the ultrasonic signal by sampling an array of receivers at sample intervals to collect a time domain return signal for each receiver. For example, the transmitter may be a transducer that is surrounded by an array of microphones for receiving the time domain return signals. The UGR system then converts each time domain return signal to a frequency domain return signal. The UGR system generates an acoustic image that includes, for each of a plurality of directions, a beamformed frequency domain return signal that approximates the frequency domain return signal from that direction. Each direction may be considered to correspond to a pixel of the acoustic image associated with a horizontal angle and a vertical angle. For example, the horizontal and vertical angles may range +/−40 degrees and the directions may be separated by 5 degrees, resulting in an acoustic image that is 17 by 17 pixels. The UGR system employs a beamforming technique to generate a beamformed frequency domain return signal by combining the frequency domain return signals of the receivers. The UGR system then generates from the acoustic image a feature image with a feature value for each direction. For example, a feature may be depth (e.g., distance to a reflection point) or intensity derived from the beamformed frequency domain return signal for a direction. The UGR system then submits the feature image to a classifier to classify the feature image as representing a certain gesture. For example, the classifier may be a deep learning system such as a convolutional neural network ("CNN") that includes a convolution layer followed by a fully connected ("FC") layer. The convolution layer may include a convolution sublayer, a rectified linear unit ("ReLU") sublayer, and a max pooling sublayer. The classifier may be trained using training data that includes feature images with labels indicating their classifications (e.g., type of gesture). When an HMD uses an ultrasonic sensor (<15 mW) with the UGR system instead of an optical sensor, the HMD would be able to support nearly 100 k gestures within the same IO energy budget as an optical sensor, as described in the Background, which is a 200-fold increase in the supported number of gestures.

In some embodiments, the UGR system recognizes dynamic gestures by sending out a sequence of ultrasonic signals and generating a feature image for each ultrasonic signal as described above. For example, if a dynamic gesture is anticipated to take three seconds, then the UGR system sends a sequence of short ultrasonic signals for a three-second duration. In such a case, the deep learning network may include a CNN along with a long short-term memory ("LSTM") layer that inputs the output of the CNN. When a sequence of feature images representing a dynamic gesture is input to the deep learning network, the LSTM layer calculates an activation value for each node of the LSTM layer. The activation value for a node is calculated based on both the current feature image and the activation value for the previous feature image. In this way, the UGR system processes the feature images of a sequence serially, factoring in the classification of each feature image of the sequence. In addition, the deep learning network may include multiple convolution layers connected in series followed by an FC layer, an LSTM layer, a softmax layer, and a mean pooling layer. The deep learning network may also be used to process in parallel sequences of feature images for multiple features such as a sequence of feature images for depth and a sequence of feature images for intensity. In such a case, the deep learning network may include a convolution layer for each feature followed by an FC layer that is fully connected to each convolution layer and followed by the LSTM layer, the softmax layer, and the mean pooling layer.

FIG. 1 is a block diagram illustrating an architecture of the UGR system in some embodiments. The UGR system includes a pulse design component 101 that generates a signal to form the chirp and sends the signal to a piezoelectric transducer 102 for generating the chirp. A microphone array 103 receives the return signals of the chirp that are reflected by a hand forming the gesture. A beamforming component 104 receives the samples of the return signals for a chirp and forms an acoustic image that may be filtered by a matched filtering component 105. A feature extraction component 106 generates a feature image from the acoustic images of a chirp. A deep classifier component 107 inputs a feature image or a sequence of feature images and outputs a classification of the gesture.

Overview of CNNs

CNNs are a type of neural network that has been developed to process images. A CNN inputs an image and outputs a classification of the image. For example, a CNN can be used to automatically determine whether a scan of a patient indicates the presence of a tumor. A CNN has multiple layers such as a convolution layer (e.g., with a convolution sublayer, an ReLU sublayer, and a pooling sublayer), an FC layer, and so on. Some more complex CNNs may have multiple convolution layers, ReLU layers, pooling layers, and FC layers.

The convolution sublayer may include multiple filters (also referred to as kernels or activation functions). A filter inputs a convolution window of an image, applies weights to each pixel of the convolution window, and outputs an activation value for that convolution window. For example, if the image is 256 by 256 pixels, the convolution window may be 8 by 8 pixels. The filter may apply a different weight to each of the 64 pixels to generate the activation value. The convolution sublayer may include, for each filter, a node (also referred to as a neuron) for each pixel of the image. Each node outputs an activation value based on a set of weights that are learned during a training phase for the CNN. For example, if an image is 256 by 256 pixels, then each filter may be associated with 65,536 nodes (i.e., 256*256). The nodes may be considered to form a 3D convolution volume with a height and width of 256 and a depth of 3 (i.e., the number of filters) with 64 weights per node. If an assumption is made that the activation value calculated for a convolution window at one location to identify a feature or characteristic (e.g., edge) would be useful to identify that feature at a different location, then all the nodes for a filter can share the same set of weights. With the sharing of weights, both the training time and the storage requirements can be significantly reduced.

The ReLU sublayer has a ReLU volume that may have a node for each node of the convolution volume with the same height, width, and depth (i.e., same number of filters). The ReLU sublayer applies a filter to each activation value of the convolution volume to generate an activation value for the ReLU volume. For example, a filter such as max(0, activation value) may be used to ensure that the activation value is not negative.

The pooling sublayer may be used to reduce the size of the ReLU volume by downsampling the ReLU volume to form a pooling volume. For example, the pooling volume may have an activation value that is an average of groups of 2 by 2 activation values of the ReLU volume. Continuing with the example above, the volume of the pooling sublayer would have 128 by 128 nodes for each filter.

The FC layer includes some number of nodes that are each connected to every node of the pooling volume. For example, if an image is to be classified as being a cat, dog, bird, mouse, or ferret, then the FC layer may include five nodes whose activation values provide scores indicating the likelihood that an image contains one of the animals. Each node has a filter with its own set of weights that are adapted to the type of the animal that the filter is adapted to classify.

Transmitter/Receiver Design and Signal Design

Figure 2:
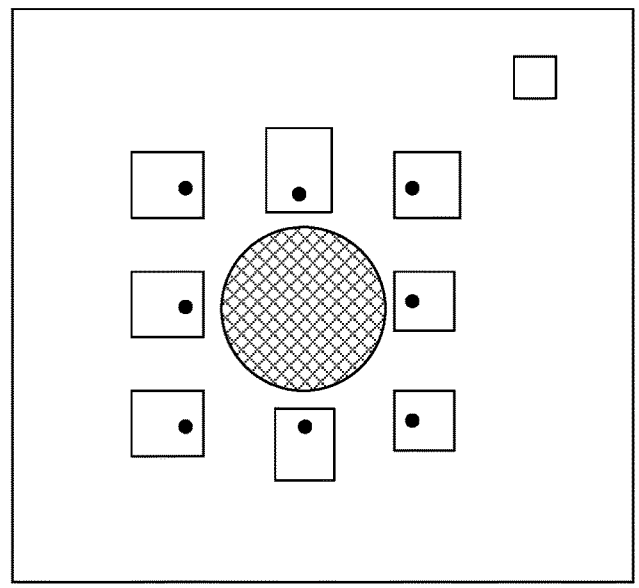
FIG. 2 is an image of a transmitter/receiver in some embodiments.

In some embodiments, the UGR system employs a transmitter/receiver that includes a transmitter and a number of receivers. The transmitter may be a piezoelectric transducer placed at the center of an 8-element array of receivers such as microelectromechanical systems ("MEMS") microphones. The transmitter/receiver is connected to an audio interface (an analog-to-digital converter and a digital-to-analog converter). The transmitter/receiver may be controlled by the same computing system that processes the return signal or by a dedicated processor that controls the transmitting and receiving. FIG. 2 is an image of a transmitter/receiver in some embodiments.

In some embodiments, the UGR system may employ an ultrasonic signal that has the following characteristics:
  (a) its auto-correlation has one sharp peak for easier detection of echoes using the cross-correlation method;
  (b) if the piezoelectric transducer resonates around 40 kHz, the transmit pulse may be band-limited to 36-44 kHz; and
  (c) the pulse is also time-limited since the width of the pulse $T_P$ should be smaller than the minimal time of flight ($ToF_{min}$) (e.g., for $d_{min}$=30 cm, $ToF_{min}$=1.7 ms).

The UGR system may employ a linear frequency modulated ("LFM") chirp that has a duration $T_P=1.5$ ms and is band-limited to 36-44 kHz. The amount of spectral leakage of the LFM chirp is inversely proportional to the duration of the chirp. The UGR system applies a rectangular filter in the frequency domain in the desired frequency range (i.e., 36-44 kHz) followed by a Hamming window in the time domain to reduce the spreading (correlations) in the autocorrelation function.

In some embodiments, the UGR system transmits a chirp periodically. The chirp may start at a frequency of 36 kHz and linearly increase to a frequency of 44 kHz over a duration of 1.5 ms. The UGR system may sample the frequency of the return signals received by each microphone at a rate of 192 kHz.

Beamforming Techniques

As described above, the UGR system generates an "acoustic image," for example, for a field of view ("FoV") of +/−40 degrees horizontally (azimuth) and vertically (elevation). The acoustic image may include a pixel for every 5 degrees. Thus, the acoustic image would be 17×17 pixels for a total of 289 pixels with each pixel representing a direction. To generate an acoustic image, the UGR system employs beamforming technology to generate, for each pixel, a beamformed frequency domain return signal with multiple frequency bins to represent a frequency domain return signal from the direction of the pixel.

In some embodiments, the UGR system samples the ultrasonic signals that are received by an m-element microphone array (e.g., m=8) and combines the signals to form a single received signal for each direction. The UGR system may employ a Minimum Variance Distortionless Response ("MVDR") beamformer ("BF") as described in J. Capon, "High-resolution frequency-wavenumber spectrum analysis," Proc. IEEE, vol. 57, no. 8, pp. 1408-1418, 1969, that follows the overall BF architecture as described in I. Tashev, Sound Capture and Processing, Practical Approaches, Wiley, UK, 1st edition, 2009, ISBN 978-0-470-31983-3. Both references are hereby incorporated by reference.

In the following, x(t, m) is a matrix that represents the amplitude received by microphone m at time t. The UGR system may start sampling the microphones prior to the expected arrival of the return signal and continue for some time longer than the length of the chirp. The UGR system converts x(t, m) to the frequency domain return signal and extracts the portion corresponding to the frequencies of the chirps as X(f, m). X(f, m) is a matrix that represents the frequency domain return signal for frequency bin f. The number of frequency bins may be 512. Y(d, f) is a matrix (e.g., the acoustic image) that represents an estimated frequency domain return signal that was received from direction d. The number of directions may be 289. The following pseudo code outlines the calculation of Y(d, f).

```
1    for d = 1, 289
2        for f = 1, 512
3            for m = 1, 8
4                Y(d, f) += X(f, m) * W(d, f, m)
5        for d = 1, 289
6            for f = 1, 512
7                W(d, f, m) = (D^H(d, f, m)C_NN^-1/D^H(d, f, m)C_nn^-1 D(d, f, m)))^T
```

W(d, f, m) is a matrix that represents a weight associated with each microphone for each direction and frequency. To generate the value for the estimated frequency domain return signal for a frequency and a direction, the UGR system generates, for each microphone, the product of the amplitude of that frequency for that microphone by the weight for that frequency and direction. The UGR system sums the products to give the value for the estimated frequency domain return signal for that frequency and that direction as illustrated by line 4 of the pseudo code. $C_{NN}^{-1}$ is a matrix (m×m) that is an inverse noise covariance matrix of the microphone array. The elements of $C_{NN}^{-1}$ are computed prior to use the UGR system based on a room similar to the operating environment of the UGR system. Since $C_{NN}^{-1}$ is not updated, the beamformer is time-invariant and can be designed offline as described in M. Thomas, H. Gamper, and I. Tashev, "BFGUI: An interactive tool for the synthesis and analysis of microphone array beamformers," in ICASSP, 2016, which is hereby incorporated by reference. During real-time operation, the UGR system need only take an inner product of the weight vector for a frequency with a vector of the values of the frequency domain return signal for that frequency to compute Y(d, f). D(d, f, m) is a matrix that for each direction and frequency represents $[1 \; e\hat{}(if(t_{d2}-t_{d1})) \; \ldots \; e\hat{}(if(t_{dM}-t_{d1}))]^H$, where i is the complex number sqrt(−1), f is the frequency, $t_{dm}$ represents the time it takes for sound to travel from the gesture in direction d to microphone m via a direct path (e.g., assuming the hand is a distance of 60 cm from the microphone), and H is the Hermitian transpose. After beamforming, the UGR system may perform a matched filtering on Y(d, f) with the chirp to maximize the signal-to-noise ratio of the time domain received signal when corrupted by white noise.

In some embodiments, the UGR system may extract features, such as of depth (time of flight) and intensity, from the estimated frequency domain return signal for each direction to generate the feature image. The UGR system extracts the depth d* by finding the peaks in the cross-correlation as represented by the following:

$$R_{XS}(\tau) = FFT^{-1}[X(f)S^*(f)]$$
$$\tau^* = \underset{\tau \in [ToF_{min}, ToF_{max}]}{\mathrm{argmax}} R_{XS}(\tau)$$
$$d^* = \frac{c\tau^*}{2}$$

The UGR system convolves each estimated frequency domain return signal with a frequency domain chirp and identifies the maximum time τ* of overlap as the depth. The intensity I* is the $L_2$ norm of the signal around τ*, i.e., $$I^* = \int_{\tau^* - \frac{T_P}{2}}^{\tau^* + \frac{T_P}{2}} |x(t)|^2 dt.$$

Classification

The recognition of a gesture by the UGR system may be considered to be a sequence learning problem. The objective is to produce a single label (or gesture) y summarizing the input sequence of feature images of a gesture for an arbitrary length input sequence $\langle x_1, x_2, \ldots, x_T \rangle$, where T is the length of the sequence. In other words, the learning problem is to estimate the function $f$ where $f : \langle x_1, x_2, \ldots, x_T \rangle \mapsto y$.

Figure 3:
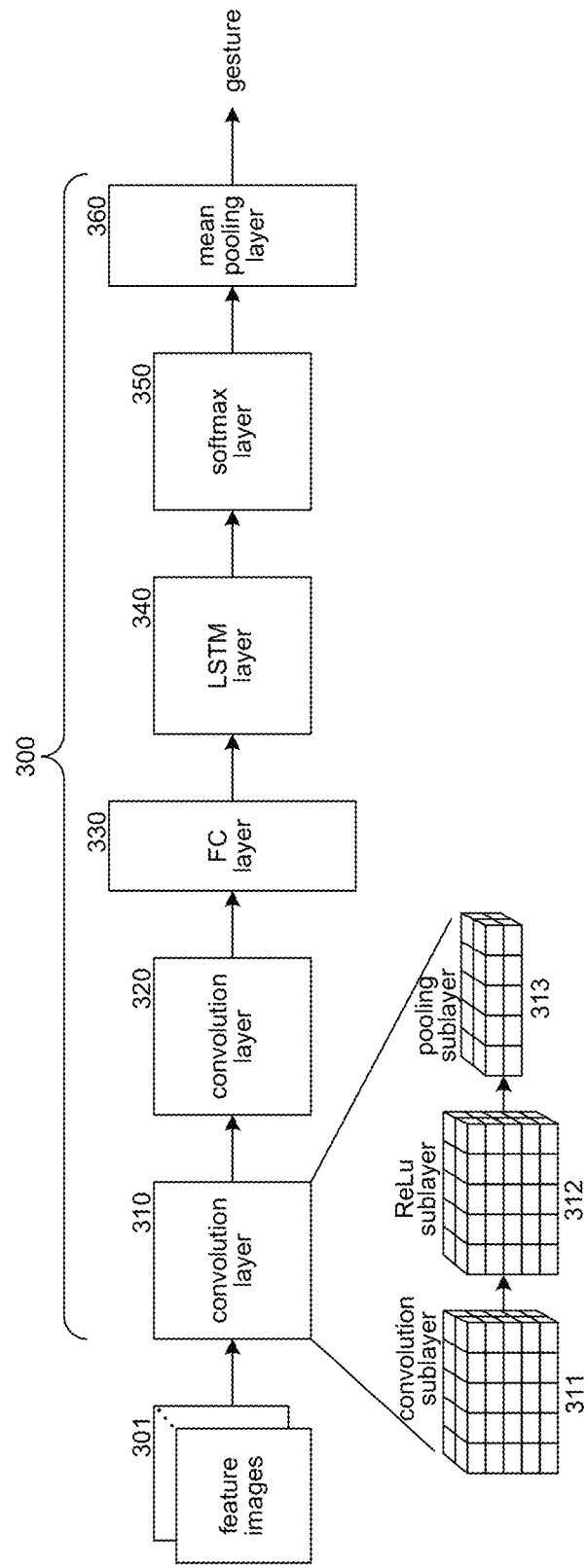
FIG. 3 illustrates the components of a CNN in some embodiments.

In some embodiments, the UGR system may use a CNN that is a combination of a CNN layer and an LSTM layer. FIG. 3 illustrates the components of a CNN in some embodiments. A CNN 300 includes a first convolution layer 310, a second convolution layer 320, an FC layer 330, an LSTM layer 340, a softmax layer 350, and a mean pooling layer 360. Each convolution layer includes a convolution sublayer 311, a ReLU sublayer 312, and a pooling sublayer 313. Feature images 301 that are input to the CNN 300 are for either depth or intensity features.

Figure 4:
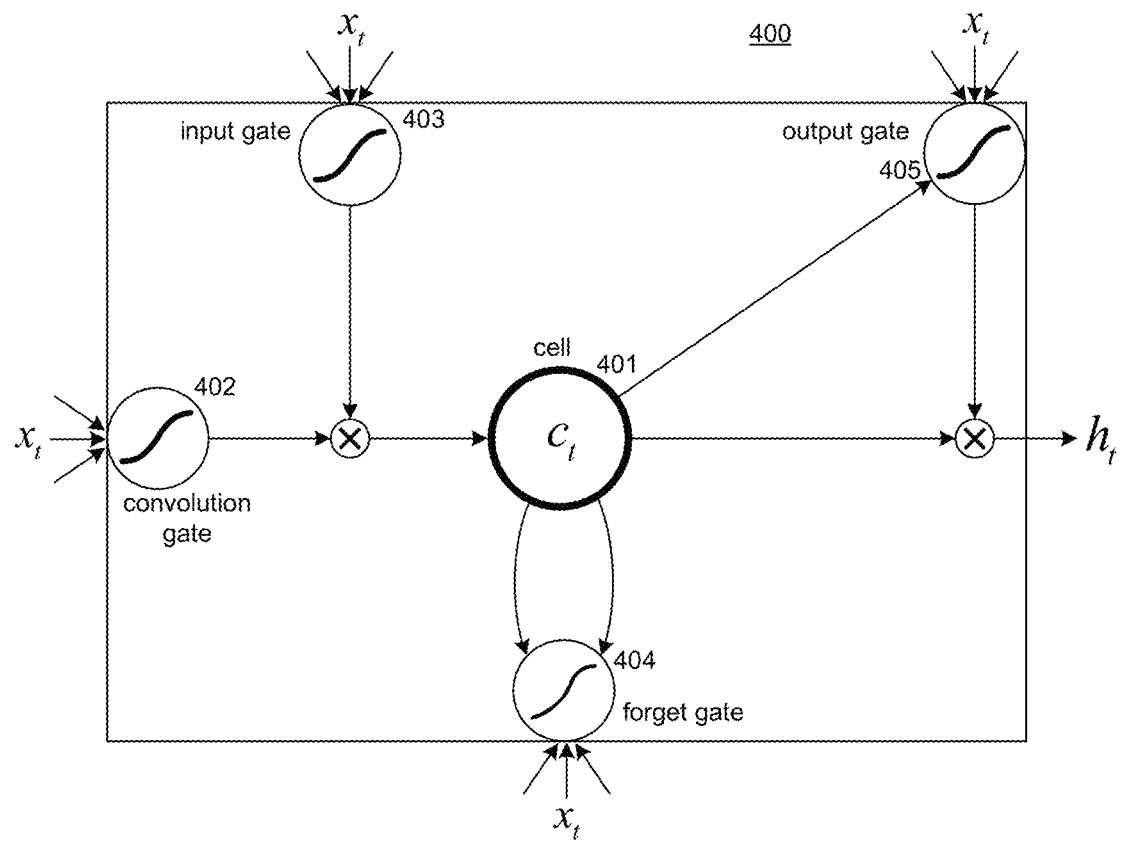
FIG. 4 is a block diagram that illustrates a dual input CNN architecture in some embodiments.

Although a feature image for depth captures depth in space, it does not capture depth in time. Since dynamic gestures evolve in both space and time, the UGR system captures additional information about temporal dynamics by incorporating temporal recurrence connections using recurrent neural networks ("RNNs"). Although RNNs have been successful in speech recognition, speech enhancement, and language modeling tasks, they are difficult to train due to the vanishing/exploding gradients problem over long time steps. The UGR system overcomes this problem using an LSTM layer that incorporates memory cells that allow the CNN to learn to selectively update or forget previous hidden states given new inputs. The UGR system may use a unidirectional left-to-right LSTM. The LSTM layer inputs the high-level features generated by the CNN to capture the temporal structure of the gesture. The temporal connections may occur only at the LSTM layer. FIG. 4 illustrates a memory cell 400 of the LSTM layer in some embodiments. A cell 401 is connected to a convolution gate 402, an input gate 403, a forget gate 404, and an output gate 405. The convolution gate inputs a window of features output by the CNN layer and applies a filter to generate a convolution value. The input gate inputs the window and the current activation value of the cell and applies a function to generate an input value. The convolution value and input value are combined (e.g., using a weighting function) to generate a value that is input to the cell. The forget gate inputs the window and the current value of the cell and applies a function to generate a forget value that is input to the cell. The cell combines the input values to generate a new current activation value. The output gate inputs the window and the new current activation value of the cell and applies a function to generate an output value. For the final classification stage, the softmax layer inputs the output of the LSTM layer.

Figure 5:
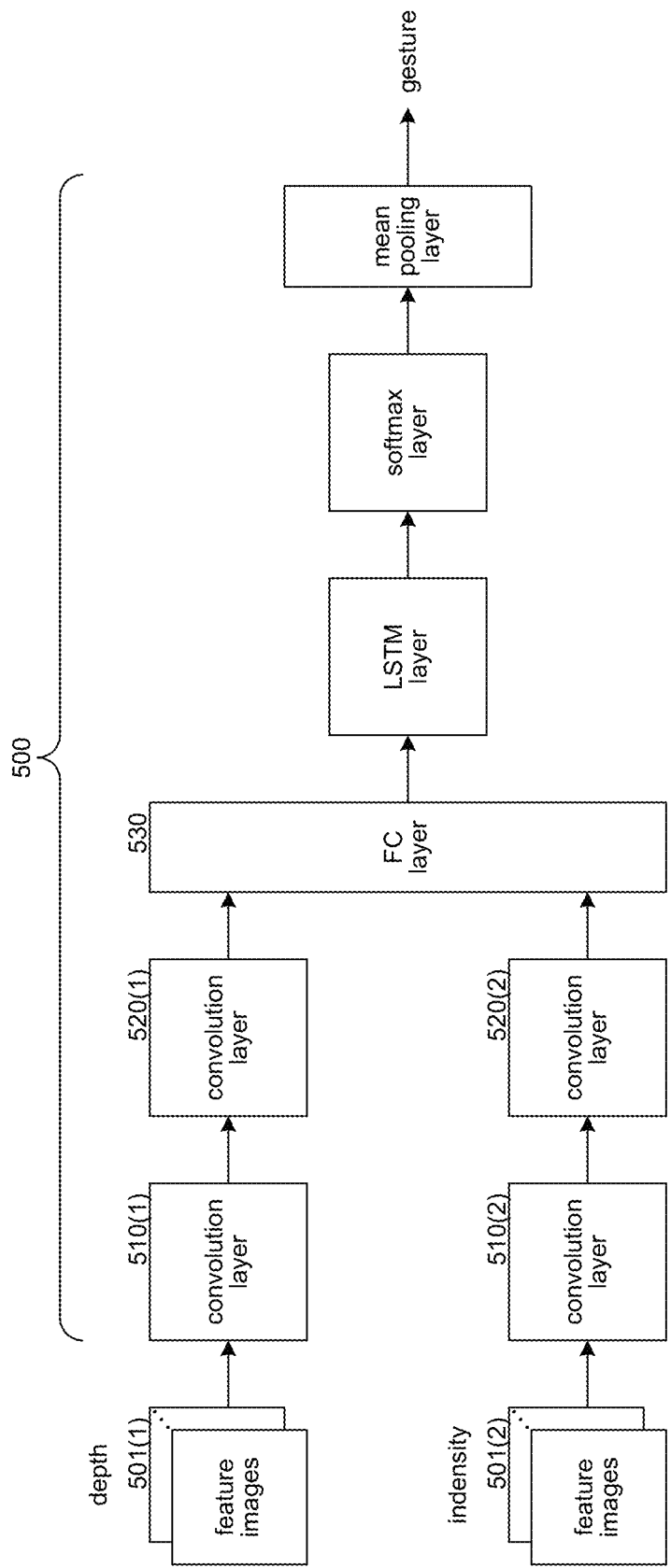
FIG. 5 illustrates a memory cell of the LSTM layer in some embodiments.

In some embodiments, the UGR system may train all weights in the CNN using supervised cross-entropy training. For every feature image $x_t$ at time step t, the CNN generates a posterior probability for gesture c, i.e., $p(\hat{y}_t=c|x_t)$, $c \in C$ where C is the set of gestures. Since the objective is to generate a single gesture for the entire sequence from t=1 to t=T, the UGR system performs a mean pooling of the posteriors of all the gestures and picks the gesture with the highest mean posterior. To improve the accuracy further, the UGR system may use both depth and intensity features, which may provide useful complementary information when used in conjunction. Thus, the UGR system may use a dual input CNN architecture. FIG. 5 is a block diagram that illustrates a dual input CNN architecture in some embodiments. FIG. 5 is similar to FIG. 3, except that separate convolution layers are for used for each feature. For a first feature, the CNN includes convolution layers 510(1) and 520(1) that input feature images 501(1) for the first feature. For a second feature, the CNN includes convolution layers 510(2) and 520(2) that input feature images 501(2) for the second feature. The outputs of the convolution layers 520(1) and 520(2) are fully connected to FC layer 530. The feature images 501(1) and 501(2) are thus processed simultaneously.

In some embodiments, the UGR system may train the CNN using a computational network toolkit "CNTK" as described in D. Yu, et al., "An Introduction to Computational Networks and the Computational Network Toolkit," Tech. Rep. Microsoft, Redmond, Wash. 2014, which is hereby incorporated by reference. The UGR system may use a depth feature and an intensity feature. For both features, the UGR system may use a 2D kernel size of 2×2. The stride lengths for both the horizontal and vertical strides may be 1. Zero-padding may be used at the image edges. These settings may be used for the convolutional layers. The UGR system may perform max pooling over small regions of size 2×2 with non-overlapping horizontal and vertical strides of length 2. The difference between the depth and intensity convolution layers is in the number of kernels. For the depth features, the UGR system may use 16 and 32 kernels for 410(1) and 420(1), respectively. For intensity features, the UGR system may use 16 kernels for both 410(2) and 420(2). The UGR system may use a dropout factor of 0.2 to improve generalization. The UGR system may use 128 as the output dimension of the FC layer.

In some embodiments, the UGR system may use context information at each time step by stacking neighboring frames along the channel. For depth features, a context window of size 5 (i.e., from t−2, . . . , t+2) may be used. Thus, at each time step, the input feature image with context may be a tensor of dimension 17×17×5 instead of a 17×17×1 tensor without context. Similarly, for intensity features, a context window of size 7 may be used.

Figure 6:
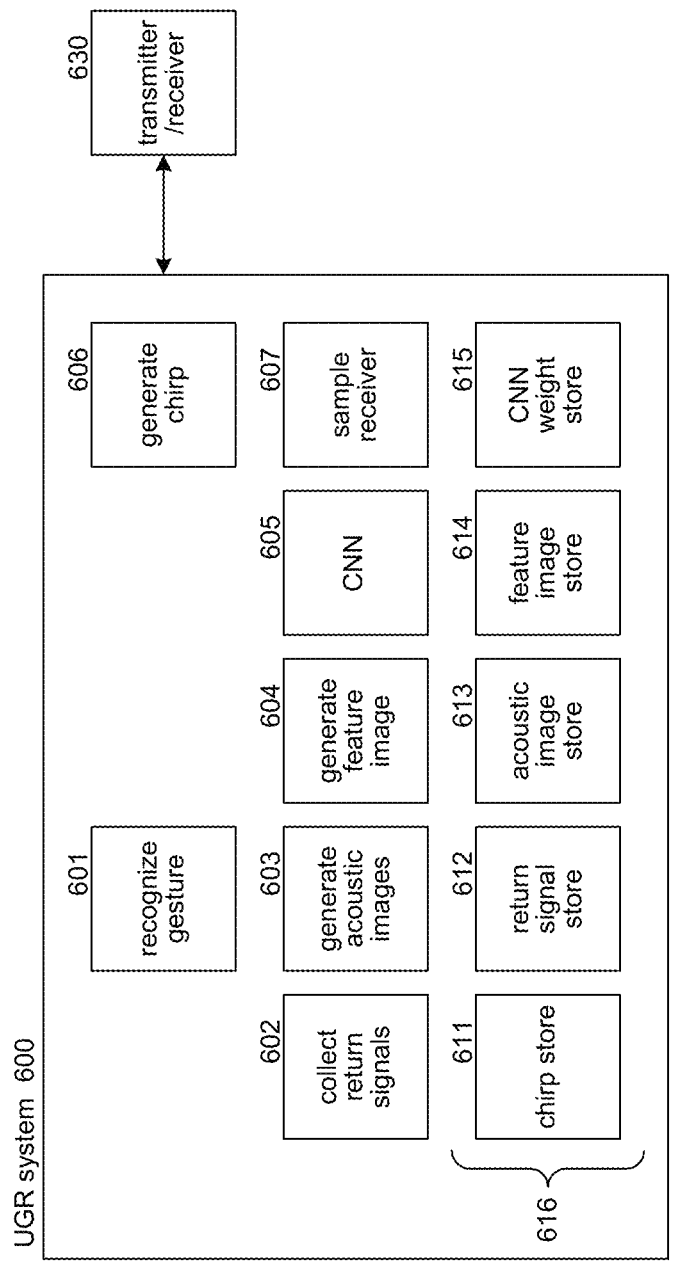
FIG. 6 is a block diagram that illustrates components of the UGR system in some embodiments.

FIG. 6 is a block diagram that illustrates components of the UGR system in some embodiments. The UGR system 600 includes a recognize gesture component 601, a collect return signals component 602, a generate acoustic images component 603, a generate feature image component 604, a CNN component 605, a generate chirp component 606, and a sample receiver component 607. The recognize gesture component controls the overall gesture recognition by invoking the other components. The generate chirp component is invoked to generate a chirp based on a specification of the chirp that is stored in a chirp store 611 and directs the chirp to be transmitted via a transmitter/receiver 630. The sample receiver component is invoked to sample the return signals from the transmitter/receiver. The collect return signals component collects the return signals for each sample and stores the return signals in a return signal store 612. The generate acoustic image component generates the acoustic images for a chirp and stores the acoustic images in an acoustic image store 613. The generate feature image component generates a feature image from the acoustic images and stores the feature image in the feature image store 614. The CNN component is invoked to recognize a gesture based on the sequence of feature images using weights learned during a training phase that are stored in a CNN weight store 615.

The computing systems on which the UGR system may be implemented may include a central processing unit, input devices, output devices (e.g., display devices and speakers), storage devices (e.g., memory and disk drives), network interfaces, graphics processing units, accelerometers, cellular radio link interfaces, global positioning system devices, and so on. The computing systems may include servers of a data center, massively parallel systems, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the UGR system. The data transmission media are used for transmitting data via transitory, propagating signals or carrier waves (e.g., electromagnetism) via a wired or wireless connection.

The UGR system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various embodiments. Aspects of the UGR system may be implemented in hardware using, for example, an application-specific integrated circuit (ASIC).

Figure 7:
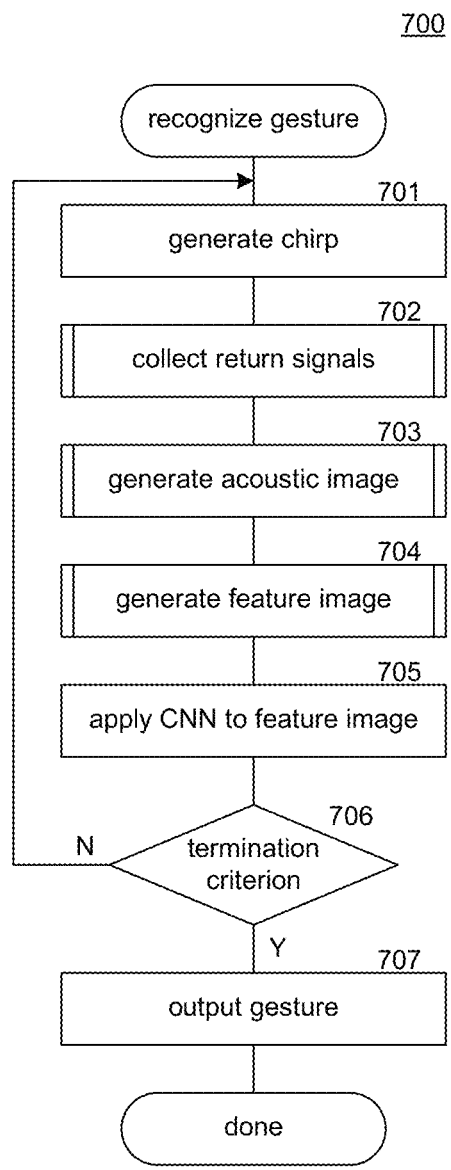
FIG. 7 is a flow diagram that illustrates processing of a recognize gesture component in some embodiments.

FIG. 7 is a flow diagram that illustrates processing of a recognize gesture component in some embodiments. A recognize gesture component 700 controls the overall recognition of a gesture. In blocks 701-706, the component loops transmitting a sequence of chirps and processing the return signals to identify a dynamic gesture. In block 701, the component invokes the generate chirp component to generate the chirp. In block 702, the component invokes the collect return signals component to collect the return signals from the chirp. In block 703, the component invokes a generate acoustic image component to generate the acoustic image for the chirp. In block 704, the component invokes the generate feature image component to generate a feature image from the sequence of acoustic images. In block 705, the component applies the CNN to the feature image. In decision block 706, if a termination criterion is satisfied (e.g., a certain number of chirps have been transmitted), then the component continues at block 707, else the component loops to block 701 to transmit the next chirp. In block 707, the component outputs the gesture that was identified by the CNN and then completes.

Figure 8:
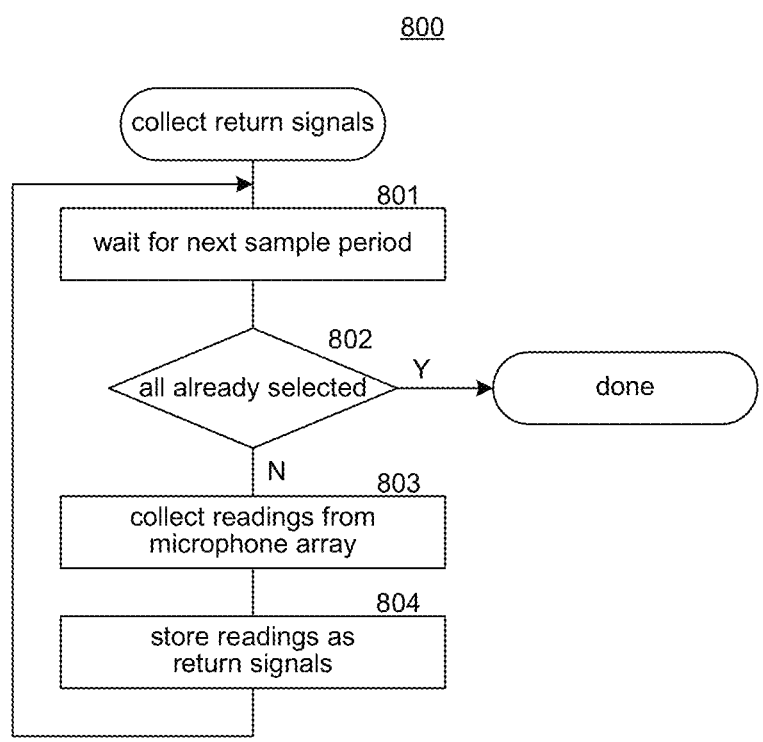
FIG. 8 is a flow diagram that illustrates processing of a collect return signals component in some embodiments.

FIG. 8 is a flow diagram that illustrates processing of a collect return signals component in some embodiments. A collect return signals component 800 is invoked to collect the return signals of a chirp. In block 801, the component waits for the next sample period. In decision block 802, if all the sample periods have already been selected, then the component completes, else the component continues at block 803. In block 803, the component collects readings from the microphone array. In block 804, the component stores the readings as return signals in the return signal store and then loops to block 801 to wait for the next sample period.

Figure 9:
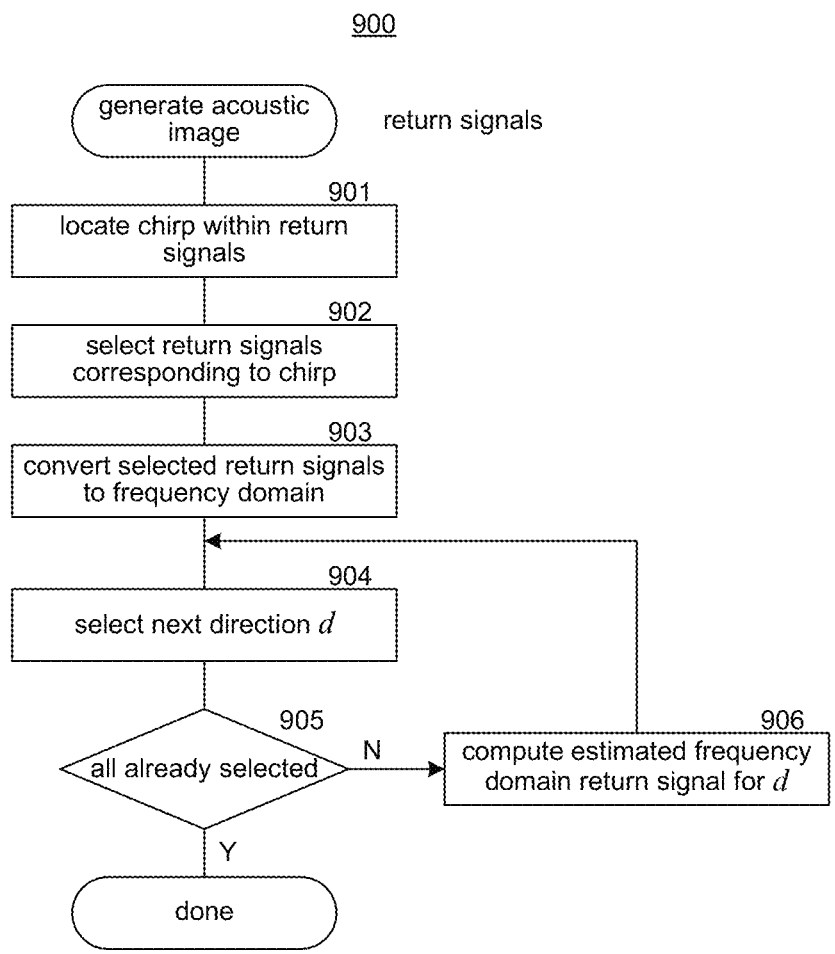
FIG. 9 is a flow diagram that illustrates the processing of a generate acoustic image component in some embodiments.

FIG. 9 is a flow diagram that illustrates the processing of a generate acoustic image component in some embodiments. A generate acoustic image component 900 is invoked to generate an acoustic image from the collected return signal for each microphone. In block 901, the component locates the chirp within the return signal of each microphone. In block 902, the component selects the return signal of each microphone corresponding to the chirp. In block 903, the component converts the return signal for each microphone from a time domain return signal to a frequency domain return signal. In block 904, the component selects the next direction d. If decision block 905, if all the directions have already been selected, then the component completes, else the component continues at block 906. In block 906, the component computes the estimated frequency domain return signal for direction d and loops to block 904 to select the next direction.

Figure 10:
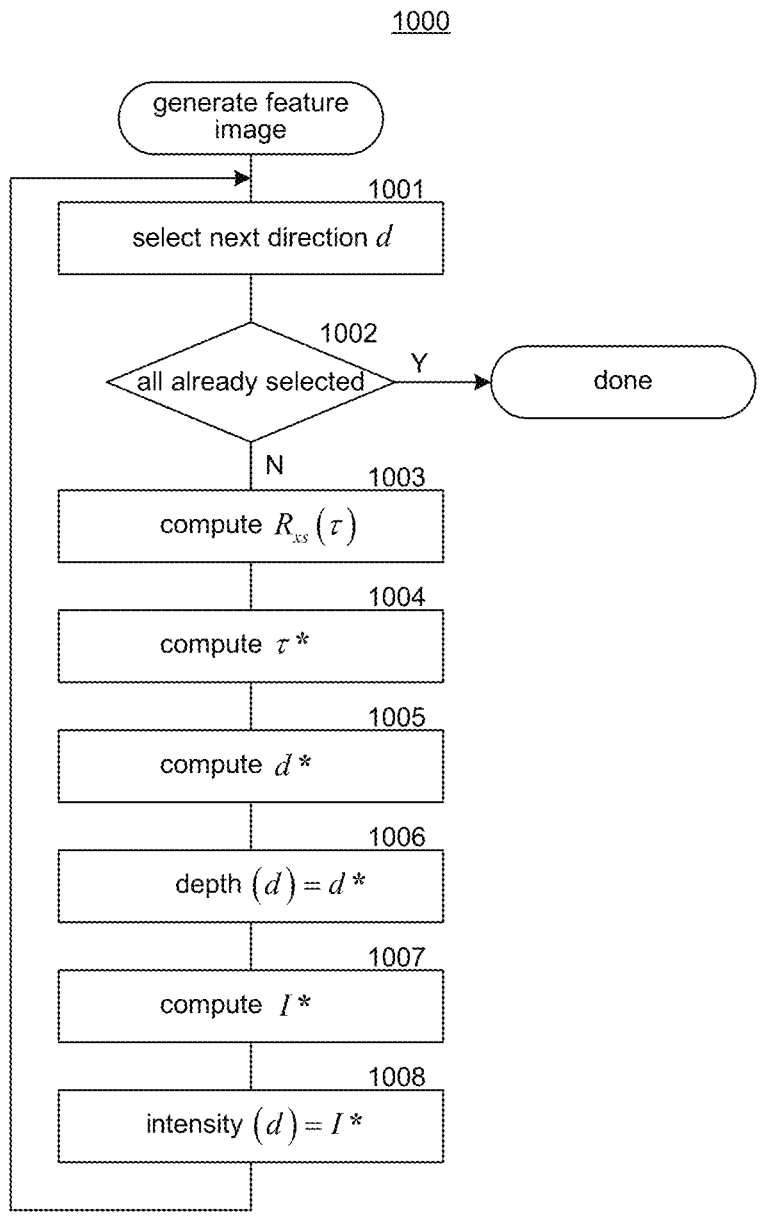
FIG. 10 is a flow diagram that illustrates the processing of a generate feature image component in some embodiments.

FIG. 10 is a flow diagram that illustrates the processing of a generate feature image component in some embodiments. A generate feature image component 1000 generates a feature image for a depth feature and an intensity feature and stores them in the feature image store. In block 1001, the component selects the next direction d. In decision block 1002, if all the directions have already been selected, then the component completes, else the component continues at block 1003. In blocks 1003-1005, the component computes the depth d* for the selected direction d. In block 1006, the component stores the depth in association with the direction in the feature image store. In block 1007, the component computes the intensity I* for the selected direction. In block 1008, the component stores the intensity in association with the selected direction in the feature image store and then loops to block 1001 to select the next direction.

The following paragraphs describe various embodiments of aspects of the UGR system. An implementation of the UGR system may employ any combination of the embodiments. The processing described below may be performed by a computing device with a processor that executes computer-executable instructions stored on a computer-readable storage medium that implements the UGR system.

In some embodiments, a method performed by a computing device for recognizing a gesture is provided. The method transmits via a transmitter an ultrasonic chirp to receive time domain return signals from the gesture. For each of a plurality of receivers, the method receives the time domain return signal by sampling that receiver at sample intervals and converts the time domain return signal to a frequency domain return signal. The method generates an acoustic image with a beamformed frequency return signal for each of a plurality of directions. The generating of the acoustic image includes performing a beamforming of the frequency domain return signals to generate a beamformed frequency domain return signal for each direction. The method generates a feature image for a feature with a feature value for each direction from the acoustic image. The method also submits the feature image to a classifier to classify the gesture. In some embodiments, the classifier is a convolutional neural network. In some embodiments, multiple chirps are transmitted in sequence and a sequence of feature images is generated with one feature image for each chirp and wherein the submitting includes submitting the sequence of feature images to the classifier to classify a dynamic gesture. In some embodiments, 4 the classifier is a convolutional neural network ("CNN"). In some embodiments, the classifier includes a convolution layer and a long short-term memory ("LSTM") layer. In some embodiments, the classifier includes multiple convolution layers, a fully connected layer, a long short-term memory ("LSTM") layer, a softmax layer, and a mean pooling layer. In some embodiments, multiple sequences of feature images are generated for multiple features and the classifier includes a convolution layer for each feature, a fully connected layer, a long short-term memory ("LSTM") layer, a softmax layer, and a mean pooling layer, wherein the fully connected layer is fully connected to the convolution layers. In some embodiments, the feature is selected from a group consisting of depth and intensity. In some embodiments, the beamforming uses a noise covariance matrix for the receivers that was generated prior to the transmitting of the chirp. In some embodiments, the generating of the acoustic image includes performing a match filtering of the beamformed frequency domain return signals and the transmitted chirp.

In some embodiments, a computing system for recognizing a gesture is provided the computing system comprises one or more computer-readable storage mediums storing computer-executable instructions and one or more processors for executing the computer-executable instructions stored in the one or more computer-readable storage mediums. The instructions include instructions of a component that accesses, for each of a plurality of ultrasonic pulses, time domain return signals that are reflections from the gesture of that transmitted ultrasonic pulse where each time domain return signal was received by a receiver. The instructions include instructions of a beamforming component that, for each ultrasonic pulse and each direction, performs beamforming to generate, from frequency domain return signals corresponding to the time domain return signals, a beamformed frequency domain return signal for that pulse and direction. The instructions include instructions of a feature extraction component that, for each ultrasonic pulse, extracts from the beamformed frequency domain return signals a feature value for a feature for each direction. The instructions include instructions of a classifier component that receives the feature values for each ultrasonic pulse, recognizes the gesture based on the feature values, and outputs an indication of the recognized gesture. In some embodiments, the classifier component implements a convolutional neural network ("CNN"). In some embodiments, the CNN includes a convolution layer and a long short-term memory ("LSTM") layer. In some embodiments, the CNN includes multiple convolution layers, a fully connected layer, a long short-term memory ("LSTM") layer, a softmax layer, and a mean pooling layer. In some embodiments, the feature extraction component extracts feature values for multiple features and the CNN includes a convolution layer for each feature, a fully connected layer, a long short-term memory ("LSTM") layer, a softmax layer, and a mean pooling layer, wherein the fully connected layer is fully connected to the convolution layers. In some embodiments, the frequency of the ultrasonic pulse varies.

In some embodiments, a method performed by a computing system for recognizing a gesture is provided. The method transmits transmitting an ultrasonic pulse. The method receives, at each of a plurality of receivers, a return signal from the ultrasonic pulse. The method performs beamforming based on the return signals to generate a beamformed return signal for each of a plurality of directions. The method generates a feature value for each beamformed return signal. The method applies a classifier to the feature values to classify the gesture. In some embodiments, the classifier is a convolutional neural network. In some embodiments, the classifier is performed by a deep learning system.

In some embodiments, a deep learning system for recognizing a gesture from feature images generated from return signals of ultrasonic pulses reflected from the gesture is provided. The deep learning system includes a first convolution layer that inputs feature images in sequence and outputs generated first features for each feature image, the first convolution layer including a first convolution sublayer, a first rectified linear unit ("ReLU") sublayer, and a first max pooling sublayer. The deep learning system also includes a second convolution layer that inputs the first features in sequence and outputs generated second features for each feature image, the second convolution layer including a second convolution sublayer, a second ReLU sublayer, and a second max pooling layer. The deep learning system also includes a fully connected layer that inputs the second features in sequence and outputs generated third features for each feature image. The deep learning system also includes a long short-term memory layer that inputs the third features in sequence and outputs fourth features for each feature image. The deep learning system also includes a softmax layer that inputs the fourth features in sequence and outputs probabilities of classifications for the sequence of feature images. The deep learning system also includes a max pooling layer that inputs probabilities of the classification and outputs an indication of the classification for the sequence of feature images.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims. Aspects of ultrasonic depth imaging are described in U.S. Patent Application No. 2016/0077206, entitled "Ultrasonic Depth Imaging," filed on Sep. 11, 2014, which is hereby incorporated by reference.

We claim:

1. A method performed by a computing device for recognizing a gesture, the method comprising:
   transmitting via a transmitter an ultrasonic chirp to receive time domain return signals from the gesture;
   for each of a plurality of receivers,
      receiving the time domain return signal by sampling that receiver at sample intervals; and
      converting the time domain return signal to a frequency domain return signal;
   generating an acoustic image with a beamformed frequency return signal for each of a plurality of directions, the generating of the acoustic image including performing a beamforming of the frequency domain return signals to generate a beamformed frequency domain return signal for each direction;
   generating a feature image for a feature with a feature value for each direction from the acoustic image; and
   submitting the feature image to a classifier to classify the gesture, wherein the classifier is a convolutional neural network ("CNN") including multiple convolution layers, a fully connected layer, a long short-term memory ("LSTM") layer, a softmax layer, and a mean pooling layer.

2. The method of claim 1 wherein multiple chirps are transmitted in sequence and a sequence of feature images is generated with one feature image for each chirp and wherein the submitting includes submitting the sequence of feature images to the classifier to classify a dynamic gesture.

3. The method of claim 1 wherein multiple sequences of feature images are generated for multiple features and the classifier includes a convolution layer for each feature, and wherein the fully connected layer is fully connected to the convolution layers.

4. The method of claim 1 wherein the feature is selected from a group consisting of depth and intensity.

5. The method of claim 1 wherein the beamforming uses a noise covariance matrix for the receivers that was generated prior to the transmitting of the chirp.

6. The method of claim 1 wherein the generating of the acoustic image includes performing a match filtering of the beamformed frequency domain return signals and the transmitted chirp.

7. A computing system for recognizing a gesture, the computing system comprising:
   one or more computer-readable storage mediums storing computer-executable instructions of:

a component that accesses, for each of a plurality of ultrasonic pulses, time domain return signals that are reflections from the gesture of that transmitted ultrasonic pulse, each time domain return signal having been received by a receiver;

a beamforming component that, for each ultrasonic pulse and each direction, performs beamforming to generate, from frequency domain return signals corresponding to the time domain return signals, a beamformed frequency domain return signal for that pulse and direction;

a feature extraction component that, for each ultrasonic pulse, extracts from the beamformed frequency domain return signals a feature value for a feature for each direction; and a classifier component that receives the feature values for each ultrasonic pulse, recognizes the gesture based on the feature values, and outputs an indication of the recognized gesture, wherein the classifier component implements a convolutional neural network ("CNN") including multiple convolution layers, a fully connected layer, a long short-term memory ("LSTM") layer, a softmax layer, and a mean pooling layer; and one or more processors for executing the computer-executable instructions stored in the one or more computer-readable storage mediums.

8. The computing system of claim 7 wherein the feature extraction component extracts feature values for multiple features and the CNN includes a convolution layer for each feature, and wherein the fully connected layer is fully connected to the convolution layers.

9. The computing system of claim 7 wherein the frequency of the ultrasonic pulse varies.

10. A method performed by a computing system for recognizing a gesture, the method comprising:
transmitting an ultrasonic pulse;
receiving, at each of a plurality of receivers, a return signal from the ultrasonic pulse;
performing beamforming based on the return signals to generate a beamformed return signal for each of a plurality of directions;
generating a feature value for each beamformed return signal; and
applying a classifier to the feature values to classify the gesture, wherein the classifier component implements a convolutional neural network ("CNN") including multiple convolution layers, a fully connected layer, a long short-term memory ("LSTM") layer, a softmax layer, and a mean pooling layer.

11. The method of claim 10 wherein the classifier is performed by a deep learning system.

12. A deep learning system for recognizing a gesture from feature images generated from return signals of ultrasonic pulses reflected from the gesture, the deep learning system comprising:
a first convolution layer that inputs feature images in sequence and outputs generated first features for each feature image, the first convolution layer including a first convolution sublayer, a first rectified linear unit ("ReLU") sublayer, and a first max pooling sublayer;
a second convolution layer that inputs the first features in sequence and outputs generated second features for each feature image, the second convolution layer including a second convolution sublayer, a second ReLU sublayer, and a second max pooling layer;
a fully connected layer that inputs the second features in sequence and outputs generated third features for each feature image;
a long short-term memory layer that inputs the third features in sequence and outputs fourth features for each feature image;
a softmax layer that inputs the fourth features in sequence and outputs probabilities of classifications for the sequence of feature images; and
a max pooling layer that inputs probabilities of the classification and outputs an indication of the classification for the sequence of feature images.

* * * * *